(12) United States Patent
Rombaut et al.

(10) Patent No.: US 10,604,463 B2
(45) Date of Patent: Mar. 31, 2020

(54) ORGANIC SOLUBILISATION AND/OR EXTRACTION SOLVENT, EXTRACTION METHOD USING SAID SOLVENT, AND EXTRACTS OBTAINED BY SAID METHOD

(71) Applicants: NATUREX, S.A., Avignon (FR); UNIVERSITE D'AVIGNON ET DES PAYS DE VAUCLUSE, Avignon (FR)

(72) Inventors: Natacha Rombaut, Saint Saturnin les Avignon (FR); Anne-Sylvie Fabiano Tixier, Rochefort du Gard (FR); Simona Birtic, Cavaillon (FR); Antoine Charles Bily, Vedene (FR); Marc Roller, Morieres les Avignon (FR); Farid Chemat, Morieres les Avignon (FR)

(73) Assignees: Naturex, S.A., Avignon (FR); Université d'Avignon et des Pays de Vaucluse, Avignon (FR)

( * ) Notice: Subject to any disclaimer, the term of this patent is extended or adjusted under 35 U.S.C. 154(b) by 0 days.

(21) Appl. No.: 15/764,941

(22) PCT Filed: Oct. 13, 2016

(86) PCT No.: PCT/FR2016/052643
§ 371 (c)(1),
(2) Date: Aug. 22, 2018

(87) PCT Pub. No.: WO2017/064424
PCT Pub. Date: Apr. 20, 2017

(65) Prior Publication Data
US 2018/0354879 A1  Dec. 13, 2018

(30) Foreign Application Priority Data

Oct. 14, 2015 (FR) ..................................... 15 59749

(51) Int. Cl.
*B01D 11/02* (2006.01)
*C07C 35/08* (2006.01)
*A23L 33/105* (2016.01)

(52) U.S. Cl.
CPC ............ *C07C 35/08* (2013.01); *A23L 33/105* (2016.08); *B01D 11/0288* (2013.01); *A23V 2002/00* (2013.01); *A61K 2236/00* (2013.01)

(58) Field of Classification Search
CPC .... C07C 35/08; A23L 33/105; B01D 11/0288
(Continued)

(56) References Cited

U.S. PATENT DOCUMENTS

| 2,302,463 A | 11/1942 | Palmer et al. |
| 2,302,468 A | 11/1942 | Palmer et al. |

(Continued)

FOREIGN PATENT DOCUMENTS

| EP | 0781842 A2 | 7/1997 | |
| FR | 2892933 A1 * | 5/2007 | ............. A61K 8/922 |

(Continued)

OTHER PUBLICATIONS

Baldasseroni et al., "Occupational Exposure to n-hexane in Italy—Analysis of a Registry of Biological Monitoring," Int Arch Occup Environ Health 76:260-266 (2003).
(Continued)

*Primary Examiner* — Deborah D Carr
(74) *Attorney, Agent, or Firm* — Pepper Hamilton LLP (57) ABSTRACT

The invention relates to a novel organic solubilisation and/or extraction solvent comprising at least one compound selected from the group of saturated monocyclic terpenoids, to an extraction method using said solvent, and to extracts obtained by said method.
More particularly, the invention relates to a novel use of para-menthane, a saturated terpenoid compound, as a solvent derived from natural substances, and also to a solvent comprising para-menthane.

6 Claims, 2 Drawing Sheets

Chemical Structure of the Solvent according to the Invention (1-isopropyl-4-methylcyclohexane)

(58) Field of Classification Search
USPC .......................................................... 554/13
See application file for complete search history.

(56) References Cited

U.S. PATENT DOCUMENTS

| | | | |
|---|---|---|---|
| 2,400,012 | A | 5/1946 | Littmann |
| 2,537,297 | A | 1/1951 | Alexander |
| 2,597,372 | A | 5/1952 | Pines et al. |
| 5,938,859 | A * | 8/1999 | Clark ................. C11D 7/24 134/11 |
| 6,872,263 | B1 | 3/2005 | Jansen et al. |
| 2004/0102351 | A1 | 5/2004 | Jansen et al. |
| 2004/0238006 | A1 | 12/2004 | Sears et al. |
| 2009/0306386 | A1 | 12/2009 | Durand et al. |
| 2011/0056694 | A1 | 3/2011 | Sears et al. |
| 2013/0281747 | A1 | 10/2013 | Chink et al. |
| 2014/0346391 | A1 | 11/2014 | Kim et al. |

FOREIGN PATENT DOCUMENTS

| | | |
|---|---|---|
| FR | 2892933 A1 | 5/2007 |
| JP | 2005/023196 A | 1/2005 |
| WO | 2012/012856 A1 | 2/2012 |

OTHER PUBLICATIONS

Karlberg et al., "Air Oxidation of d-limonene (the Citrus Solvent) Creates Potent Allergens," Contact Dermatitis 26:332-340 (1992).

Li et al., "Measurement and Modelling of the Solubility of Carbon Dioxide in Aqueous 1,8-p-menthane-diamine Solution," J Chem. Thermodynamics 71:64-70 (2014).

Shuikin et al., "Selective Demethylation of n-Alkanes Over a Skeletal Nickel-Aluminum Catalyst," Bulletin of the Academy of Sciences of the USSR, Division of Chemical Science 6(7):907-909 (1957).

Sicaire et al., "2-Methyltetrahydrofuran: Main Properties, Production Processes, and Application in Extraction of Natural Products," In: Alternative Solvents for Natural Products Extraction, Chemat and Vian, eds., Springer-Verlag (2014), Chapter 12, pp. 253-268.

Thomas et al., "Limonene," Natural Product Reports 6:291-309 (1989).

Turek et al., "Stability of Essential Oils: A Review," Comprehensive Reviews in Food Science and Food Safety 12:40-53 (2013).

Manini et al., "Liquid Chromatography—Mass Spectrometry in Occupational Toxicology: A Novel Approach to the Study of Biotransformation of Industrial Chemicals," Journal of Chromatography A 1058:21-37 (2004).

PCT International Search Report corresponding to PCT/FR2016/052643, dated Jan. 30, 2017

* cited by examiner

Chemical Structure of the Solvent according to the Invention (1-isopropyl-4-methylcyclohexane)

Figure 1

σ-profile of hexane and p-menthane

ORGANIC SOLUBILISATION AND/OR EXTRACTION SOLVENT, EXTRACTION METHOD USING SAID SOLVENT, AND EXTRACTS OBTAINED BY SAID METHOD

This application is a national stage application under 35 U.S.C. § 371 of PCT Application No. PCT/FR2016/052643, filed Oct. 13, 2016, which claims priority of France Patent Application No. 1559749, filed Oct. 14, 2015.

BACKGROUND OF THE INVENTION

The present invention relates to a novel organic extraction and/or solubilisation solvent comprising at least one compound selected from the group of saturated monocyclic terpenoids, to an extraction method using said solvent, and to extracts obtained by said method.

More particularly, the invention relates to a novel use of para-menthane, a saturated monocyclic terpenoid compound, as a solvent derived from natural substances, and is also directed to a solvent comprising para-menthane.

A further object of the invention is to define an extraction and solubilisation method using said solvent, especially in liquid/liquid or solid/liquid extraction methods, as well as extracts obtained by carrying out this method.

The solvent according to the invention can be used for the extraction and/or solubilisation of plant and/or animal and/or prokaryotic biological material.

Preferably, said solvent will be used for the extraction and solubilisation of active natural compounds from a plant extract or from plant matter of natural origin.

Active natural compounds are molecules obtained from a plant material which have an activity of biological and technological interest. These active natural compounds can be in pure form or contained in extracts. Active natural compounds belong to the category of pigments, including carotenoids and chlorophylls, flavourings, including terpenes, and plant oils, including triglycerides or phospholipids. These active compounds can be used in food, cosmetic, pharmaceutical and nutraceutical applications.

The expression "natural compounds" refers to various categories of biochemical compounds. Apart from plant fats, small amounts of these compounds are usually present in plant matrices. A distinction is thus made between several categories of natural compounds according to their chemical nature:

Pigments: can be present in the form of partially hydroxylated carbon chains containing an aromatic ring. Lipophilic pigments can be obtained by concentration of extracts obtained from plants called oleoresins. Pigments are distinguished according to their colour, for example: carotenoids (yellow, orange or red colour), anthocyanins (red to violet or even blue colour), xanthophylls and curcuminoids (yellow colour), chlorophylls (green colour) and phycocyanin (blue colour).

Flavourings: this category of compounds refers to volatile compounds which are present in essential oils, concretes and absolutes of flowers, for example. Molecules of the terpene type (their chemical structure is composed of an aromatic ring containing hydroxyl groups) constitute a large proportion of the flavourings. The aromatic profiles of plants are dominated by a number of terpenes, depending on the plants. For example, basil essential oil is composed mainly of linalool, estragole, eugenol and methyl eugenol.

Plant oils: these mixtures contain compounds of which the main chemical structure is a carbon chain typically having 14 to 20 carbon atoms (the units forming the fats are called fatty acids) and an unsaponifiable fraction (polar lipids, sterols, etc.). Plant oils are lipophilic compounds and extracts containing fats are in the form of oil or solid fatty plant material containing triglycerides or phospholipids.

The procedure that is most widely used for obtaining natural compounds is solid/liquid extraction. There are a number of conventional methods of solid/liquid extraction, such as maceration, percolation, lixiviation and decoction. Traditionally, these methods use water and ethanol to obtain natural extracts. However, these solvents permit the solubilisation mainly of hydrophilic compounds with low selectivity.

Other solvents are used for a more selective extraction. The solvents that are most widely used in the extraction of natural substances are organic solvents such as hexane, methanol, dichloromethane and acetone. These solvents are very effective substances which dissolve solid and liquid solutes, and their volatility facilitates their removal at the end of the method. However, a large number of organic solvents are also flammable, very volatile and toxic (carcinogenic, mutagenic, etc.). A number of works have already been carried out on their harmful effects (Baldasseroni et al., 2003; Manini et al., 2004). In addition, the gradual depletion of oil resources and increasing regulatory constraints are encouraging a trend towards alternative solvents. Thus, many studies aim more particularly to replace hexane with other solvents which would allow an equivalent extraction yield to be obtained and which would be less harmful.

Hexane is a molecule which is classified in the category of "carcinogenic, mutagenic and reprotoxic" (CMR) molecules of class 3 (EU CMR list), that is to say as a reprotoxic molecule. The physico-chemical characteristics of hexane make it dangerous to handle. Hexane has a low flash point (23.3° C.) and an auto-ignition temperature of 233.9° C.

Various solvents have been proposed to replace hexane.

Plant oils can be used as an extraction solvent for non-volatile compounds. The enrichment of the oils is then limited by the solubility of the plant extracts in the oil, permitting only partial extraction of the natural compounds contained in the treated plants. Agro-solvents of the methyl-THF type have been used for extraction (Sicaire et al., 2014), but the main industrial constraint is based on the reactivity of 2-methyl-THF with plastics materials.

Other agro-solvents of the terpene type obtained from co-products of the agri-food industry have been proposed for the extraction of natural compounds. Terpene solvents such as limonene or alpha-pinene (for example WO 2007/057549 A2) can have chemical reactivity due to the presence of double bonds. Thomas and Bessière (1989) show the existence of numerous conversions of limonene following chemical reactions, for example of the acid-base, epoxidation, hydrogenation and oxidation type. Limonene therefore constitutes a species which is reactive in solution. The conversions of limonene involve a modification of its structure by rearrangement and reaction of the double bonds with other chemical species present in solution.

It is known from Karlberg et al. (1992) that limonene, when exposed to air, undergoes auto-oxidation reactions which lead to the formation of oxygenated derivatives of the hydroperoxide type. The compounds formed are, moreover, allergenic. In addition, the auto-oxidation reaction of terpenoids (such as limonene, thymol, citral and alpha-pinene, for example) leads to the production of free radicals (Turek and Stintzing, 2013), which can react with the target extraction compounds, resulting in the degradation thereof.

Figure 1:
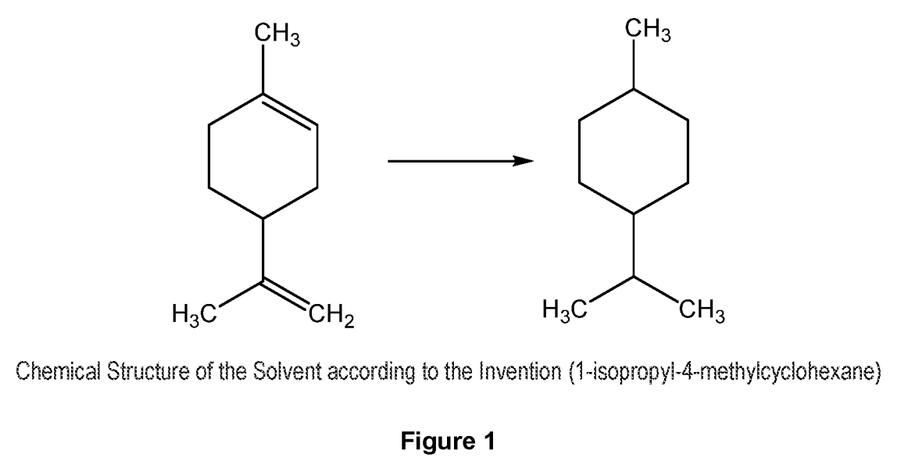
FIG. 1 shows the chemical structure of the solvent according to the invention (1-isopropyl-4-methylcyclohexane).

In order to remedy the disadvantages of terpene compounds containing double bonds, it is possible to consider a terpene analogue that does not contain double bonds. Several teams of chemists mention obtaining a molecule called para-menthane (1-isopropyl-4-methylcyclohexane, FIG. 1) by catalytic hydrogenation (US 2013/0281747 A1 of Chink et al., 2013, Li et al., 2014, Shuikin and Cherkashin, 1957).

Para-menthane has been mentioned in various patents.

Para-menthane has been mentioned for chemical applications, especially as a compound formed during reactions or as a reagent. Accordingly, U.S. Pat. No. 2,400,012 A describes a process for obtaining para-cymene by catalytic dehydrogenation. This reaction leads to the formation of a mixture composed of para-cymene and para-menthane. In this invention, the para-menthane formed is reused for the purpose of recycling in the dehydrogenation reaction. Para-menthane is used in another invention (U.S. Pat. Nos. 2,302,463 and 2,302,468) in a liquid-phase reaction with oxygen. There is described therein a reaction aimed at converting para-menthane in order to obtain alcohols, aldehydes, ketones and acids. A process for sulfurisation of terpenes is described in U.S. Pat. No. 2,537,297. The sulfurisation is carried out on mixtures of terpenes, which can include para-menthane. U.S. Pat. No. 2,597,372 describes obtaining cyclopentane hydrocarbons and benzenoid hydrocarbons by reacting para-menthane and isocamphane in the presence of a palladium-type catalyst. Accordingly, since these inventions refer to the presence of para-menthane in chemical conversion reactions, they do not relate to the solvation properties of para-menthane with respect to natural compounds of interest.

Para-menthane has been proposed as a component of a mixture for removing inks (JP2005023196). The use of cleaning mixtures containing, inter alia, para-menthane has been described by the company Refining Oils in several patents (US20040102351, US20040238006 and U.S. Pat. No. 6,872,263). The inventors found a formulation of a cleaning agent comprising a saturated monocyclic terpene compound and a non-ionic surfactant. This mixture is used by being injected into a vapour phase circulating in the pipes and containers to be cleaned. In a later patent of Refining Oils (US20110056694) there is described a method for removing paraffins and bitumens in oil refining processes. The cleaning agent described is composed of para-menthane with or without an additive of the surfactant type. The spectrum of action of this agent is aimed at non-natural apolar compounds of very high molecular weight and additionally functions in a process using this mixture in the vapour state. A terpene-based formulation similar to the patents cited hereinbefore is referred to in EP 0781842 A2. This latter patent describes a non-liquid cleaning mixture composed of from 90% to 96.5% of a halogenated compound (n-propyl bromide), from 0 to 6.5% terpene compounds and from 3.5 to 5% compounds having a low boiling point. This chemical cleaning agent is used in the vapour phase at temperatures of about 70° C. to dissolve mineral oils, silicone oils or metals. In all these inventions, which are aimed at describing cleaning processes, there is no mention of the use of para-menthane for the extraction and solubilisation of natural compounds obtained from natural plant materials.

Accordingly, para-menthane has been mentioned for chemical applications or as a component of mixtures in cleaning processes. There is a continued need to identify alternative solvents to replace hexane that allow targeted natural compounds to be extracted or specifically solubilised, while obtaining at least identical yields.

SUMMARY OF THE INVENTION

The present invention relates to a novel organic extraction and/or solubilisation solvent comprising at least one compound selected from the group of saturated monocyclic terpenoids, to an extraction method using said solvent, and to extracts obtained by said method.

Preferably, at least one of the compounds selected from the group of saturated monocyclic terpenoids is para-menthane.

DETAILED DESCRIPTION DESCRIPTION OF THE INVENTION

In a preferred embodiment, the present invention aims to define a novel use of a compound, para-menthane, as an extraction solvent for plant and/or animal and/or prokaryotic biological material, and preferably as an extraction solvent from plant matrices of natural origin or as a solubilisation solvent for natural compounds. In particular, the inventors have found that para-menthane can be used in methods for the extraction and solubilisation of the main categories of natural biological compounds such as lipids, antioxidants, flavourings and fragrances, and colourings.

Among the above-mentioned natural compounds of interest there is the category of odorous molecules of the terpene type, which form part of the composition of essential oils, colourings of the carotenoid or chlorophyll type or other lipophilic colouring compounds, and fatty acids. The solvent according to the invention can be used for the extraction of all these molecules in the form of plant extracts present in plant material of natural origin. Accordingly, the extracts can be natural flavourings, oleoresins, oils or fats of plant origin.

In greater detail, the natural biological compounds include: fatty acids, lipids, oils, saponifiable compounds, unsaponifiable compounds, phytosterols, phenols, tocopherols, tocotrienols, the forms of vitamin E, vitamins, monoterpenes, diterpenes, triterpenes and saturated or unsaturated terpenoid-type compounds, aromatic compounds, flavourings and taste modifiers, perfumes, fragrances, odorous compounds, essential oils, sesquiterpenes, phenolic compounds including phenolic acids, esters and mono-phenolic compounds, flavonoids, tannins, coumarins, stilbenes, lignans, secoiridoids, isoflavones, phytic acids, phenolic alcohols, as well as saponins, antioxidants, carotenoids, chlorophylls, xanthophylls, curcuminoids, betalains, colourings, pigments, alkaloids, phenylpropanoids, biocides, antimicrobial compounds, proteins and enzymes.

The invention accordingly relates to a novel use of para-menthane as an extraction solvent, said solvent being obtained from natural raw material, with the aim of carrying out an extraction method which is more respectful of the environment, while allowing extraction yields to be obtained which are equivalent to those obtained with hexane.

The solvent according to the invention can accordingly be used for the extraction and solvation of natural biological compounds of interest that are present in liquid phase or contained, for example, in a plant matrix of natural origin.

Para-menthane constitutes a base skeleton of the terpenoids forming essential oils or other odorous compounds. The inventors have noted that traces of para-menthane can be found in some plants. Accordingly, one of the desired characteristics of a solvent is that said solvent must be as inert as possible and must not be reactive in solution, either during the extraction process or during its storage in a vessel. A solvent composed of molecules that do not contain double bonds, such as the solvent according to the invention, meets this constraint.

A person skilled in the art knows that alkanes (such as para-menthane) have a very stable carbon chain, with σ bonds, which is very difficult to break without using extreme temperature and pressure conditions in the presence of specific catalysts. He also knows that alkenes are less stable and more reactive owing to the presence of unsaturated bonds: the presence of one or more π double bonds forms a double bond which is more reactive and less stable than the σ bond.

The extraction and/or solubilisation solvent for plant and/or animal and/or prokaryotic biological material according to the invention is characterised in that it comprises at least one compound selected from the group of saturated monocyclic terpenoids. More particularly, the solvent according to the invention comprises para-menthane as the saturated monocyclic terpenoid. And preferably, but without implying any limitation, the solvent comprises at least 99% para-menthane. In such a case, impurities and oxidation-reaction-initiating compounds represent less than 1% of the solvent according to the invention.

In particular extraction modes, it may be necessary to obtain an extract in pure form. It is then necessary to remove the solvent according to the invention in order to obtain extracts that are free of solvent. Said solvent can be removed by various methods:

- by evaporation under vacuum: in this embodiment, injection of ethanol or water into the solvent according to the invention will permit the formation of an azeotropic mixture and will thus lead to evaporation at a temperature below the boiling point of said solvent alone;
- by molecular distillation under high vacuum.

In addition, because the solvent according to the invention is composed of an inert molecule, it can easily be recycled for other extractions without the formation of oxidation compounds.

The present invention also relates to a method for extracting active compounds from biological materials, especially of plant origin, in a single phase. The inventors have found that the solvent according to the invention can be used for the extraction and solubilisation of heat-sensitive compounds. Surprisingly, the extraction yields are close to those obtained with hexane, and the solvent according to the invention permits infinite solubilisation of miscible pure compounds. In addition, the solvent can be used at low temperature.

The extraction method according to the invention is perfectly compatible with the extraction of natural biological compounds such as phenolic compounds including phenols, phenolic acids and esters, mono-phenolic compounds, flavonoids, tannins, coumarins, stilbenes, lignans, secoiridoids, isoflavones, phytic acids, phenolic alcohols, as well as antioxidants, carotenoids, alkaloids, phenylpropanoids, monoterpenes, diterpenes, triterpenes and saturated or unsaturated terpenoid-type compounds, sesquiterpenes, flavourings and taste modifiers, essential oils, perfumes, fragrances, odorous compounds, aromatic compounds, biocides, antimicrobial compounds, proteins, enzymes, chlorophylls, xanthophylls, curcuminoids, betalains, colourings, pigments, phytosterols, fatty acids, tocopherols, tocotrienols, the forms of vitamin E, vitamins, lipids, oils, saponifiable compounds and unsaponifiable compounds, including saponins.

This extraction method is characterised by a procedure comprising the following successive steps:

(a) bringing a plant and/or animal and/or prokaryotic biological material or matrix, ground or unground, into contact with the solvent as described in the invention and/or with a mixture of this solvent with other solvents, then (b) separating residual solid from the plant and/or animal and/or prokayrotic biological material or matrix, (c) then partially or completely removing the solvent as described in the invention and/or the mixture of this solvent with other solvents.

The extraction will preferably be carried out from a plant matrix or material of natural origin.

In another embodiment, the solvent according to the invention can be used for solubilising more specifically lipophilic or partially polar compounds in liquid/liquid extraction operations.

The paragraphs below describe, without implying any limitation, a detailed example of the implementation of the extraction method according to the invention.

The extraction is carried out from raw material of plant origin obtained from different parts of a plant. The parts can be seeds, rhizomes, roots, tubers, stems, leaves, flowers, bark. All or parts of a plant can be subjected to an extraction, on their own or in a mixture. Preparation of the plant can involve any single operation aimed at facilitating the extraction, such as drying, grinding, flattening or flocculation.

For use in extraction methods, the solvent according to the invention can be used in pure form or in a mixture with other solvents which are miscible therein. The following sections describe in detail the extraction method to which the present invention relates.

In Step (a):

The solvent according to the invention can be used in conventional operations for extracting plant matrices of natural origin, operations such as maceration (with or without a mechanical stirring means), percolation, lixiviation, as well as in extraction methods assisted by innovative technologies such as ultrasound and microwaves.

The plant material will preferably be in ground form so that it is in the form of fragments of fine to medium particle size in order to facilitate the extraction step. The fresh plant material will advantageously have a water content of from 40 to 90 wt. %, preferably from 80 to 90 wt. %.

The plant solid/liquid ratio can be between 1/1 and 1/50 (mass by volume) and preferably 1/20 in terms of mass by volume. The extraction temperature can be between 20° C. and 150° C. However, for active compounds of natural origin, moderate temperatures are preferably used in order not to alter the structure of these compounds. The temperature would then advantageously be between 40 and 60° C. The extraction time depends on the plant material treated. The extraction time can be between 5 minutes and several hours. The inventors have not noted any change in the solvent (change in appearance or properties) after 6 hours' extraction. The extraction operation can take place at atmospheric pressure as well as at pressures greater than atmospheric pressure in order to carry out pressurised extractions. The solvent according to the invention can thus be used in single methods or operations performed at a pressure equal to or greater than atmospheric pressure.

In Step (b):

The residual solid materials are removed from the solvent by a solid/liquid separation method. This step can be carried out by filtration in order to recover the solvent according to the invention enriched with extracted compounds of interest.

In Step (c):

The solvent according to the invention can be removed from the solubilised extract by various methods:

- by evaporation under vacuum: in this embodiment, the injection of ethanol or water into the solvent according to the invention will permit the formation of an azeotropic mixture and will thus lead to evaporation at a temperature below the boiling point of the solvent according to the invention alone;
- by molecular distillation under high vacuum.

At the end of this step, an extract that is free of solvent is obtained. In addition, the solvent according to the invention recovered following the extraction remains stable because it does not contain a double bond. Its high boiling point (168° C.) also means that its volatility is much lower than that of hexane. The losses of solvent are thus minimised with the solvent according to the invention.

The invention also relates to extracts obtained after the extraction method has been carried out with the solvent according to the invention.

These extracts can be used for the manufacture of a nutraceutical composition or of a dietary or food product, or of a food supplement, or of a pharmaceutical composition or of a cosmetic composition, for oral or parenteral administration, as applicable, or for topical application.

The solvent according to the invention allows compounds of lipophilic nature or partially polar compounds to be solubilised and extracted. Accordingly, the profile of compounds extracted with this solvent may differ from hexane or any other type of apolar solvent. The extract obtained with the solvent according to the invention will therefore have a unique profile. This latter point can be illustrated in the following examples.

This invention thus demonstrates the value of using a novel solvent composed of para-menthane of 99% purity. The extraction and the solubilisation of target natural compounds by the solvent according to the invention are effective at moderate temperatures. The extraction of heat-sensitive compounds is thus made possible; such as odorous molecules of the terpene type, which form part of the composition of essential oils, colourings of the carotenoid or chlorophyll type or other lipophilic colouring compounds, and fatty acids.

In addition, the chemical structure of the solvent confers reactional stability thereon and shows extraction and solubilisation capabilities similar to those of hexane. Finally, due to the high boiling point of the solvent according to the invention, the use thereof leads to smaller losses of solvent than with hexane. Accordingly, examples illustrating the use of the solvent according to the invention are explained in detail in the following sections.

Materials and Methods

The liquid extracts obtained are analysed directly by chromatography in order to quantify the natural bioactive compounds present in solution after extraction.

Assay of Beta-Carotene

The identification and quantification of beta-carotene are carried out by high-performance liquid chromatography (HPLC). For this purpose, an analytical standard was used (beta-carotene, UV>98%, Extrasynthese, reference 0303 S), and a calibration curve was established. The HPLC instrument (Agilent 1100) is equipped with a diode array detector. Elution is carried out in isocratic conditions at 25° C., by the mobile phase composed of the mixture acetonitrile/methanol (with 0.6% ammonium acetate)/dichloromethane (77/20/3, v/v/v). The solvents are of HPLC grade. The column used is of the C18 type (150×3.0 mm—3 μm). Detection of the beta-carotene is carried out at 464 nm.

Assay of the Fatty Acids in Rapeseed Oil

The identification and quantification of the fatty acids in rapeseed oil are carried out by gas phase chromatography (GC). The instrument used (GC 3800 VARIAN) is equipped with an FID detector. The column used is of the DB23 60 m×0.26 mm type with a film having a thickness of 0.25 μm. The column is placed in an oven subjected to an initial temperature of 120° C. for 5 minutes. The temperature is increased to 200° C. (at 5° C./min) and then maintained for one minute. Finally, the temperature is increased to 230° C. (at 2°/min) and then maintained for 15 minutes. The vector gas is helium at a constant pressure of 30 psi.

Injection of the sample is carried out at 250° C. with a split of 1 to 50. Detection is carried out by an FID detector at 300° C. The fatty acids present are identified by comparison of the retention times of a mixture of fatty acids standards (Supelco 37 component FAME mix, Sigma-Aldrich, ref. CMR47885). The compounds present are recorded as the relative percentage expressed based on the total amount of the detected compounds.

Assay of the Aromatic Compounds in Basil Essential Oil

The identification of the aromatic compounds contained in basil essential oil is carried out by gas phase chromatography (GC). The instrument used (GC 7890 Agilent) is equipped with an FID detector. The column used is of the VF-MAX 30 m×0.25 mm type with a film having a thickness of 0.25 μm. The following temperature gradient of the oven in which the column is placed was used (Table 1). The vector gas is helium at a constant flow rate of 1.1 ml/min.

TABLE 1

| Temperature (° C.) | Increase (° C./min) | Temperature maintenance time (min) | Total time (min) |
| --- | --- | --- | --- |
| 60 | 0.0 | 1.0 | 1 |
| 240 | 3.0 | 5.0 | 66 |

Injection of the sample is carried out at 250° C. with a split of 1 to 100. Detection is carried out by an FID detector at 250° C. The compounds present are recorded as the relative percentage expressed based on the total of the detected compounds.

The following examples illustrate the implementation of the present invention. These examples are not limiting in any way.

EXAMPLES

Example 1

Solubility of Beta-Carotene in the Solvent Defined in the Invention in Comparison with the Solubility of Beta-Carotene in Hexane The solubility of beta-carotene is compared in two solvents: in hexane, on the one hand, and in the solvent according to the invention, on the other hand. For each solvent evaluated, 20 mg of beta-carotene, of purity greater than or equal to 97%, are brought into contact with 1 ml of solvent. The whole is placed in a flask under constant rotation at a speed of 200 rpm at 25° C. for 1 hour. The mixture is then centrifuged in order to precipitate the beta-carotene that has not been solubilised in the tested solvent. The concentration of beta-carotene in the supernatant phase thus obtained is determined by HPLC at a wavelength of 464 nm. The concentration of beta-carotene (expressed as a percentage by weight) in hexane is 0.101 and the concentration of beta-carotene in the solvent according to the invention is 0.102%.

Example 2

Solubility of Carvone in the Solvent Defined in the Invention in Comparison with the Solubility of Carvone in Hexane The solubility of carvone is compared in two solvents: in hexane, on the one hand, and in the solvent according to the invention, on the other hand. For each solvent evaluated, 1 ml of carvone, of purity greater than or equal to 99%, is dissolved with 1 ml of solvent. The whole is placed in a flask under constant rotation at a speed of 200 rpm at 25° C. for 1 hour. After the stirring phase, the carvone-hexane and carvone-solvent mixtures according to the invention are visually compared (Table 3).

TABLE 3

| | Solubilisation of carvone in hexane | Solubilisation of carvone in the solvent according to the invention |
|---|---|---|
| Visual examination | complete | complete |

The solvent according to the invention permits total solubilisation of carvone at a ratio of 1/1 and 2/1 (volume/volume): no phase separation was noted.

Example 3

Solubility of Linalool in the Solvent Defined in the Invention in Comparison with the Solubility of Linalool in Hexane The solubility of linalool is compared in two solvents: in hexane, on the one hand, and in the solvent according to the invention, on the other hand. For each solvent evaluated, 1 ml of linalool, of purity greater than or equal to 97%, is dissolved with 1 ml of solvent. The whole is placed in a flask under constant rotation at a speed of 200 rpm at 25° C. for 1 hour. After the stirring phase, the linalool-hexane and linalool-solvent mixtures according to the invention are visually compared (Table 4).

TABLE 4

| | Solubilisation of linalool in hexane | Solubilisation of linalool in the solvent according to the invention |
|---|---|---|
| Visual examination | complete | complete |

The solvent according to the invention permits total solubilisation of linalool at a ratio of 1/1 and 2/1 (volume/volume): no phase separation was noted.

Example 4

Solubility of Limonene in the Solvent Defined in the Invention in Comparison with the Solubility of Limonene in Hexane The solubility of limonene is compared in two solvents: in hexane, on the one hand, and in the solvent according to the invention, on the other hand. For each solvent evaluated, 1 ml of limonene, of purity greater than or equal to 93%, is dissolved with 1 ml of solvent. The whole is placed in a flask under constant rotation at a speed of 200 rpm at 25° C. for 1 hour. After the stirring phase, the limonene-hexane and limonene-solvent mixtures according to the invention are visually compared (Table 5).

TABLE 5

| | Solubilisation of limonene in hexane | Solubilisation of limonene in the solvent according to the invention |
|---|---|---|
| Visual examination | complete | complete |

The solvent according to the invention permits total solubilisation of limonene at a ratio of 1/1 and 2/1 (volume/volume): no phase separation was noted.

Example 5

Solubility of Estragole in the Solvent Defined in the Invention in Comparison with the Solubility of Estragole in Hexane The solubility of estragole is compared in two solvents: in hexane, on the one hand, and in the solvent according to the invention, on the other hand. For each solvent evaluated, 1 ml of estragole, of purity greater than or equal to 98%, is dissolved with 1 ml of solvent. The whole is placed in a flask under constant rotation at a speed of 200 rpm at 25° C. for 1 hour. After the stirring phase, the estragole-hexane and estragole-solvent mixtures according to the invention are visually compared (Table 6).

TABLE 6

| | Solubilisation of estragole in hexane | Solubilisation of estragole in the solvent according to the invention |
|---|---|---|
| Visual examination | complete | complete |

The solvent according to the invention permits total solubilisation of estragole at a ratio of 1/1 and 2/1 (volume/volume): no phase separation was noted.

Example 6

Solubility of Rapeseed Oil in the Solvent Defined in the Invention in Comparison with the Solubility of Rapeseed Oil in Hexane The solubility of rapeseed oil is compared in two solvents: in hexane, on the one hand, and in the solvent according to the invention, on the other hand. For each solvent evaluated, 1 ml of sunflower oil is dissolved with 1 ml of solvent. The whole is placed in a flask under constant rotation at a speed of 200 rpm at 25° C. for 1 hour. After the stirring phase, the sunflower oil-hexane and sunflower oil-solvent mixtures according to the invention are visually compared (Table 7).

TABLE 7

|  | Solubilisation of sunflower oil in hexane | Solubilisation of sunflower oil in the solvent according to the invention |
|---|---|---|
| Visual examination | complete | complete |

The solvent according to the invention permits total solubilisation of sunflower oil at a ratio of 1/1 and 2/1 (volume/volume): no phase separation was noted.

Example 7

Extraction of Rapeseed Oil from Rapeseed According to the Invention in Comparison with an Extraction Method Using Hexane Rapeseed (*Brassica napus* L.) contains from 35 to 45% oil. The fatty acid profile of industrial rapeseed oil is dominated by oleic acid (C18:1, approximately 60%, g per 100 g).

Extraction is carried out by maceration of 2 g of rapeseed, previously ground, in 20 ml of the solvent according to the invention (plant material/solvent ratio: 1/10). Maceration is carried out at 50° C., for 6 hours, in a flask under constant rotation at 200 rpm. The solid plant particles are separated from the extraction solvent by filtration. In order to obtain samples of identical volume and in order to compare the extracts, the filtrate is introduced into a vial and then the volume is made up to 20 ml with the original solvent.

The same extraction procedure can be carried out with hexane (reference solvent).

The fatty acid profile of rapeseed oil, extracted by this method, is analysed by gas phase chromatography coupled to a flame ionisation detector. The results are presented in Table 8. The proportions of fatty acids present in the extract are indicated in g per 100 g.

TABLE 8

| Nature of the fatty acid | Hexane | Solvent according to the invention |
|---|---|---|
| Palmitic acid (C16:0%) | 4.6 | 4.7 |
| Stearic acid (C18:0%) | 1.76 | 0 |
| Oleic acid (C18:1%) | 58.19 | 58.97 |
| Linoleic acid (C18:2%) | 19.23 | 19.79 |
| Linolenic acid (C18:3%) | 7.16 | 6.6 |
| Gadoleic acid (C20:1%) | 2.1 | 0 |

For the majority of fatty acids, the oil extracted with the solvent according to the invention has a proportion equivalent to that extracted with hexane.

Example 8

Extraction of Odorous Compounds from Basil Leaves According to the Invention

Basil leaves contain essential oil which is characterised by the presence in the majority of terpene compounds such as linalool, estragole, eugenol and methyl eugenol.

Extraction is carried out by maceration of 2 g of basil leaves, previously ground, in 20 ml of the solvent according to the invention (plant material/solvent ratio: 1/10). Maceration is carried out at 50° C., for 6 hours, in a flask under constant rotation at 200 rpm. The solid plant particles are separated from the extraction solvent by filtration. In order to obtain samples of identical volume and in order to compare the extracts, the filtrate is introduced into a vial and then the volume is made up to 20 ml with the original solvent.

The profile of terpene compounds obtained by analysis by gas phase chromatography coupled to a flame ionisation detector is presented in Table 9. The proportions of terpene compounds present in the extract are indicated in g per 100 g.

TABLE 9

| Nature of the compound | Solvent according to the invention |
|---|---|
| Limonene (%) | 0.70 |
| Eucalyptol (%) | 0.97 |
| trans-b-Ocimene (%) | 0.10 |
| Camphor (%) | 0.33 |
| Linalool (%) | 3.69 |
| Bergamotene (%) | 0.10 |
| b-Caryophyllene (%) | 0.19 |
| Terpinen-4-ol (%) | 0.35 |
| Estragole (%) | 7.25 |
| Methyl eugenol (%) | 0.49 |
| tau-Cadinol (%) | 0.90 |
| Eugenol (%) | 0.14 |

The solvent according to the invention permits the extraction of odorous compounds present in basil leaves.

Example 9

COSMO-RS Simulation and Physical Properties of the Solvent

Figure 2:
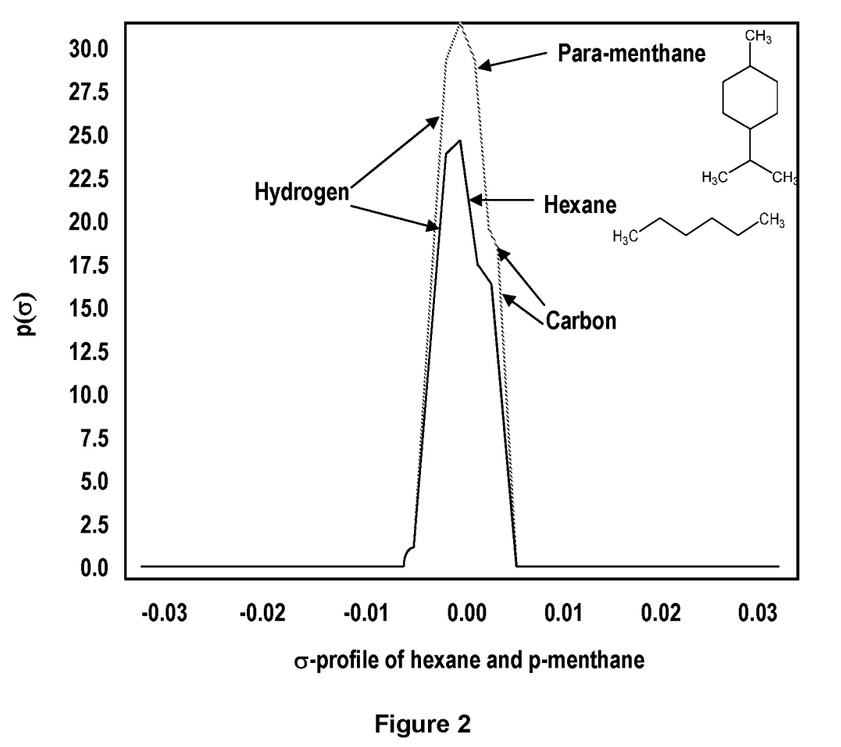
FIG. 2 shows the σ profile of hexane and of p-menthane.

The simulation approach is carried out using COSMO-RS software (FIG. 2: σ profile of hexane and of p-menthane). The molecule is immersed in a perfect conductor, which generates a charge distribution about the molecule.

FIG. 2 shows the σ profile of hexane and of p-menthane. This charge distribution is segmented and reduced to a histogram, called the σ profile. The σ profile allows a molecule to be characterised in its most stable energy state. The σ profiles of hexane and of p-menthane are similar. Their σ profile gives a broad double peak centred at σ=0, that is to say they do not have electrostatic moments. The two peaks result from the contribution of the hydrogen atoms (σ<0) and the contribution of the carbon atoms (σ>0). There is no major difference between the profile of hexane and that of p-menthane, apart from a small difference in the height of the peaks, which is due to their respective carbon and hydrogen numbers.

Figure 3:
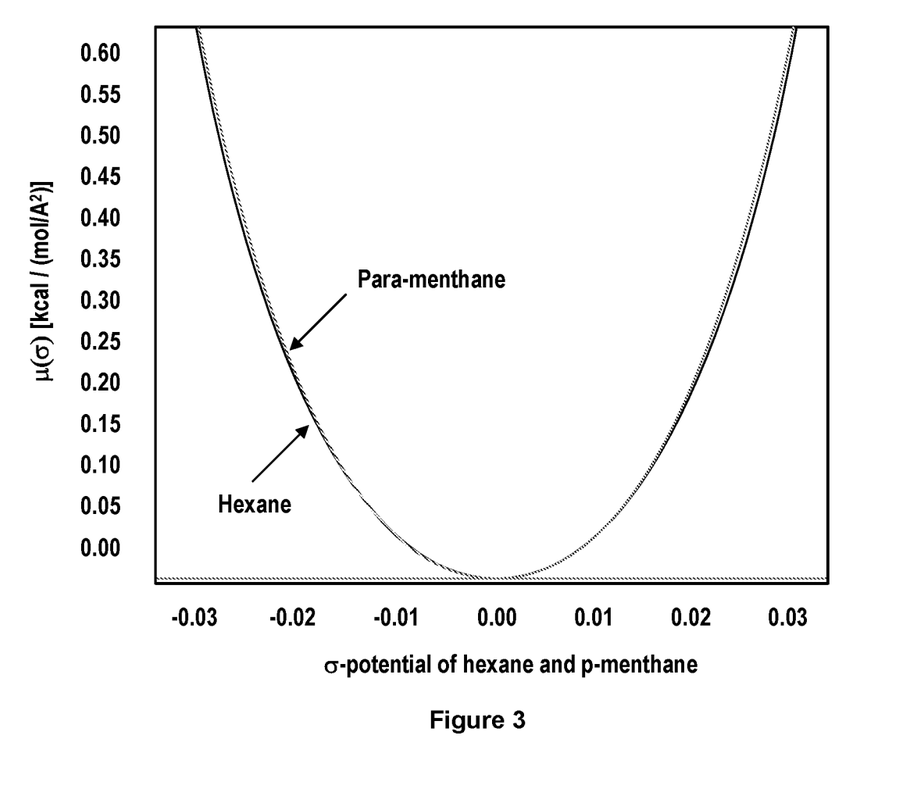
FIG. 3 shows the σ potential of hexane and of p-menthane.

FIG. 3 shows the σ potential of hexane and of p-menthane.

Calculation of the σ potentials (FIG. 3) takes account of the molecular interactions, which allows a solvent to be characterised. Here, the σ potentials are parabolas centred at σ=0, which expresses the fact that the alkanes have no affinity for positive or negative charge densities, reflecting their apolar nature. The superposition of the two potentials allows the relative index of similarity between the two curves to be calculated. At 25° C., the two molecules have 95% similarity. The solvent according to the invention appears to be a promising solvent to replace hexane, which is traditionally used in the field of extraction.

Finally, the physico-chemical data are compared in Table 10 (these data were obtained by simulation using ACD/lab software).

TABLE 10

| | n-Hexane | p-Menthane |
|---|---|---|
| Empirical formula | $C_6H_{14}$ | $C_{10}H_{20}$ |
| Density | 0.7 ± 0.1 | 0.8 ± 0.1 |
| Boiling point (° C.) | 68.5 ± 3.0 | 168.2 ± 7.0 |
| Vapour pressure at 25° C. (mmHg) | 150.9 ± 0.1 | 2.2 ± 0.1 |
| Enthalpy of vaporisation (kJ/mol) | 28.9 | 38.8 ± 0.8 |
| Flash point (° C.) | −23.3 | 44.7 ± 11.7 |
| Refractive index | 1.384 | 1.431 |
| Log P | 3.94 | 5.25 |
| Molar volume ($cm^3$) | 127.6 ± 3.0 | 178.6 ± 3.0 |
| Surface tension (dyne/cm) | 20.3 ± 3.0 | 23.9 ± 3.0 |

The flash point of the solvent according to the invention is higher than that of hexane; the solvent according to the invention thus has lower flammability than hexane. Moreover, the two solvents differ mainly by their boiling point and vapour pressure. Hexane evaporates at a lower temperature than the solvent according to the invention. The boiling point of the solvent according to the invention is close to that of terpene compounds (168° C.), and it is possible to evaporate the solvent according to the invention:

- by evaporation under vacuum: in this embodiment, injection of ethanol or water into the solvent according to the invention will permit the formation of an azeotropic mixture and will thus lead to evaporation at a temperature below the boiling point of the solvent according to the invention alone;
- by molecular distillation under high vacuum.

In addition, the solvent according to the invention, when recovered following the extraction, remains stable because it does not contain a double bond. Its high boiling point (168° C.) also means that its volatility is much lower than that of hexane. The losses of solvents are thus minimised with the solvent according to the invention.

The invention claimed is:

1. An extraction and/or solubilisation solvent for plant and/or animal and/or prokaryotic biological material, characterised in that it comprises at least one saturated monocyclic terpenoid: para-menthane.

2. The extraction and/or solubilisation solvent according to claim 1, characterised in that it comprises at least 99% para-menthane.

3. A method for extracting natural biological compounds using the solvent according to claim 1, characterised in that the method comprises the following steps:
   (a) bringing a plant and/or animal and/or prokaryotic biological material or matrix, ground or unground, into contact with said solvent and/or with a mixture thereof with other solvents, then
   (b) separating residual solid from the plant and/or animal and/or prokaryotic biological material or matrix, and
   (c) then partially or completely removing said solvent and/or the mixture thereof with other solvents.

4. The method for extracting natural biological compounds according to claim 3, characterised in that the biological material brought into contact with the solvent is a biological plant material or matrix of natural origin.

5. The method for extracting natural biological compounds according to claim 3, wherein the extracted natural biological compound is selected from fatty acids, lipids, oils, saponifiable compounds, unsaponifiable compounds, phytosterols, phenols, tocopherols, tocotrienols, forms of vitamin E, vitamins, monoterpenes, diterpenes, triterpenes and saturated or unsaturated terpenoid-type compounds, aromatic compounds, flavourings and taste modifiers, perfumes, fragrances, odorous compounds, essential oils, sesquiterpenes, phenolic compounds including phenolic acids, esters and mono-phenolic compounds, flavonoids, tannins, coumarins, stilbenes, lignans, secoiridoids, isoflavones, phytic acids, phenolic alcohols, saponins, antioxidants, carotenoids, chlorophylls, xanthophylls, curcuminoids, betalains, colourings, pigments, alkaloids, phenylpropanoids, biocides, antimicrobial compounds, proteins and enzymes.

6. The method according to claim 3, wherein said solvent comprises at least 99% para-menthane.

* * * * *